(12) United States Patent
Baugh et al.

(10) Patent No.: US 8,491,850 B2
(45) Date of Patent: Jul. 23, 2013

(54) DIAGNOSTIC TEST READER WITH LOCKING MECHANISM

(75) Inventors: Brenton Arthur Baugh, Palo Alto, CA (US); Robert Sean Murphy, Sunnyvale, CA (US)

(73) Assignee: Alverix, Inc., San Jose, CA (US)

( * ) Notice: Subject to any disclaimer, the term of this patent is extended or adjusted under 35 U.S.C. 154(b) by 1025 days.

(21) Appl. No.: 11/313,091

(22) Filed: Dec. 19, 2005

(65) Prior Publication Data
US 2007/0141696 A1 Jun. 21, 2007

(51) Int. Cl.
*G01N 33/00* (2006.01)

(52) U.S. Cl.
USPC ........... 422/401; 422/402; 422/500; 422/560; 422/561

(58) Field of Classification Search
USPC ................... 422/50, 55, 68.1, 82.05, 99, 401, 422/402, 500, 560, 561
See application file for complete search history.

(56) References Cited

U.S. PATENT DOCUMENTS

| | | | | |
|---|---|---|---|---|
| 5,304,468 | A | * | 4/1994 | Phillips et al. .................. 435/14 |
| 5,504,013 | A | | 4/1996 | Senior |
| 5,580,794 | A | | 12/1996 | Allen |
| 5,837,546 | A | | 11/1998 | Allen et al. |
| 5,872,713 | A | * | 2/1999 | Douglas et al. ................ 702/85 |
| 5,945,345 | A | | 8/1999 | Blatt et al. |
| 6,009,632 | A | * | 1/2000 | Douglas .......................... 33/562 |
| 6,187,269 | B1 | | 2/2001 | Lancesseur et al. |
| 6,235,241 | B1 | | 5/2001 | Catt et al. |
| 6,451,619 | B1 | | 9/2002 | Catt et al. |
| 6,514,461 | B1 | | 2/2003 | Lappe et al. |
| 6,716,393 | B2 | | 4/2004 | Lappe et al. |
| 6,964,752 | B2 | | 11/2005 | Lappe et al. |
| 2002/0081233 | A1 | * | 6/2002 | Lappe et al. ............... 422/82.05 |
| 2002/0114735 | A1 | * | 8/2002 | Markart ....................... 422/68.1 |
| 2004/0166023 | A1 | | 8/2004 | Lappe et al. |
| 2005/0074362 | A1 | | 4/2005 | Lappe et al. |
| 2005/0101032 | A1 | | 5/2005 | Blatt et al. |

OTHER PUBLICATIONS

The ClearBlue Easy Pregnancy Test, http://www.clearplan.com/theclearblueeasydigitalpregancytest.cfm, pp. 1-3.
Clearblue Digital Pregnancy Test—the world's first ever digital pregnancy test, http://www.unipath.com/ClearblueDigital.cfm, pp. 1-2.
eScreen! http://www.escreen.com/Page/ereader_2.html, www.escreen.com/Page/ecup_2.html, www.escreen.com/Page/featuresandbenefits_2.html, pp. 1-5.

* cited by examiner

*Primary Examiner* — Sam P Siefke
(74) *Attorney, Agent, or Firm* — K&L Gates LLP

(57) ABSTRACT

A diagnostic test reader includes an assay interface, a locking mechanism, and a test unit. The assay interface is configured to receive a diagnostic assay. The locking mechanism is configured to lock the diagnostic assay within the assay interface in response to one of the diagnostic assay and the diagnostic test reader being given a first push in a first direction toward the other of the diagnostic assay and the diagnostic test reader. The locking mechanism is also configured to unlock the diagnostic assay within the assay interface in response to the one of the diagnostic assay and the diagnostic test reader being given a second push in the first direction. The test unit is configured to analyze the diagnostic assay.

17 Claims, 6 Drawing Sheets

DIAGNOSTIC TEST READER WITH LOCKING MECHANISM

BACKGROUND

Patient samples are often analyzed for the presence of analytes to determine if a patient is carrying a disease, has an infection, has been using drugs, etc. that may or may not be present in a patient's body. Analytes are typically detected with immunoassay testing using antigen-antibody reactions. Conventionally, such tests have been performed in specialized laboratories using relatively expensive reading equipment. However, the need for on-site examination at the point-of-care, such as hospitals, emergency rooms, nursing homes, practitioner offices, and even the home of the patient, is growing rapidly. Due to the expense and size of many laboratory test readers used to analyze such tests, conventional test readers are not generally suitable for use at the point of care.

Due to the limited sensitivity and breath of available point-of-care tests, turn around time of clinically significant diagnostic test results typically requires several days time. More specifically, tests must be completed at a central laboratory or be transferred to the laboratory where they are placed in a queue to be analyzed on one of a first-in, first-out or level of emergency basis. The delay of clinically significant test results may result in the delay of treatment until the presence of a particular ailment or level of a particular condition has been verified. For example, in an embodiment where a patient experiences the onset of a sore throat, a streptococcus (strep) screen is typically performed. Currently available rapid diagnostic, point-of-care test kits lack the sensitivity to detect an early stage of strep, and therefore, the patient typically waits two to three days for strep throat test results. Since doctors typically will not prescribe antibiotics or other remedies until the presence of strep has been verified in the patient, the recovery of the patient will be delayed and, in the meantime, the patient may come in contact with and infect a number of other individuals. Concerns are magnified in cases involving more serious medical conditions in which delayed treatment can have devastating effects.

As noted above, conventional point-of-care tests kits generally lack the sensitivity to detect conditions in early stages of development. This lack of sensitivity is due in part to the relatively low price points required for point-of-care testing. More specifically, point-of-care test kits have generally incorporate manual aliquot and manual read of the results. However, manual assay reading typically results in an increased error rate. In particular, in a pregnancy test using a lateral flow assay, the color of the lateral flow assay changes if the particular pregnancy hormone human chorionic gonadotropin, or HCG, is detected. In early stages of pregnancy, levels of HCG may be significantly lower than in later levels of pregnancy. Therefore, the lower levels of HCG will result in a less noticeable color change of the lateral flow assay than for a test completed when HCG levels are at a higher concentration. Since the human eye cannot readily differentiate between small color changes in the lateral flow assay, a user may mis-read the lateral flow assay therefore providing erroneous results, such as a false negative. The lack of sensitivity in point-of-care tests further increases dependency upon tests analyzed in the central laboratory.

In view of the above, a need exists for a point-of-care immunoassay test reader incorporating non-manual methods of immunoassay analysis with lower reading error rates. By lowering error rates, delayed treatment can be decreased or prevented. This prevention is important as delayed treatment may often lead to increased progression of an ailment, increased contamination levels of new individuals having contact with the patient, and other undesired effects. In addition, a need exists for such test readers that are not only increasingly sensitive and reliable, but that also can be provided at the low price points generally required for point-of-care equipment.

SUMMARY

One aspect of the present invention relates to a diagnostic test reader including an assay interface, a locking mechanism, and a test unit. The assay interface is configured to receive a diagnostic assay. The locking mechanism is configured to lock the diagnostic assay within the assay interface in response to one of the diagnostic assay and the diagnostic test reader being given a first push in a first direction toward the other of the diagnostic assay and the diagnostic test reader. The locking mechanism is also configured to unlock the diagnostic assay within the assay interface in response to the one of the diagnostic assay and the diagnostic test reader being given a second push in the first direction. The test unit is configured to analyze the diagnostic assay.

BRIEF DESCRIPTION OF THE DRAWINGS

Embodiments of the invention are better understood with reference to the following drawings. Elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "above," "over," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following Detailed Description, therefore, is not to be taken in a limiting sense, and the scope of the present invention is defined by the appended claims.

Figure 1:
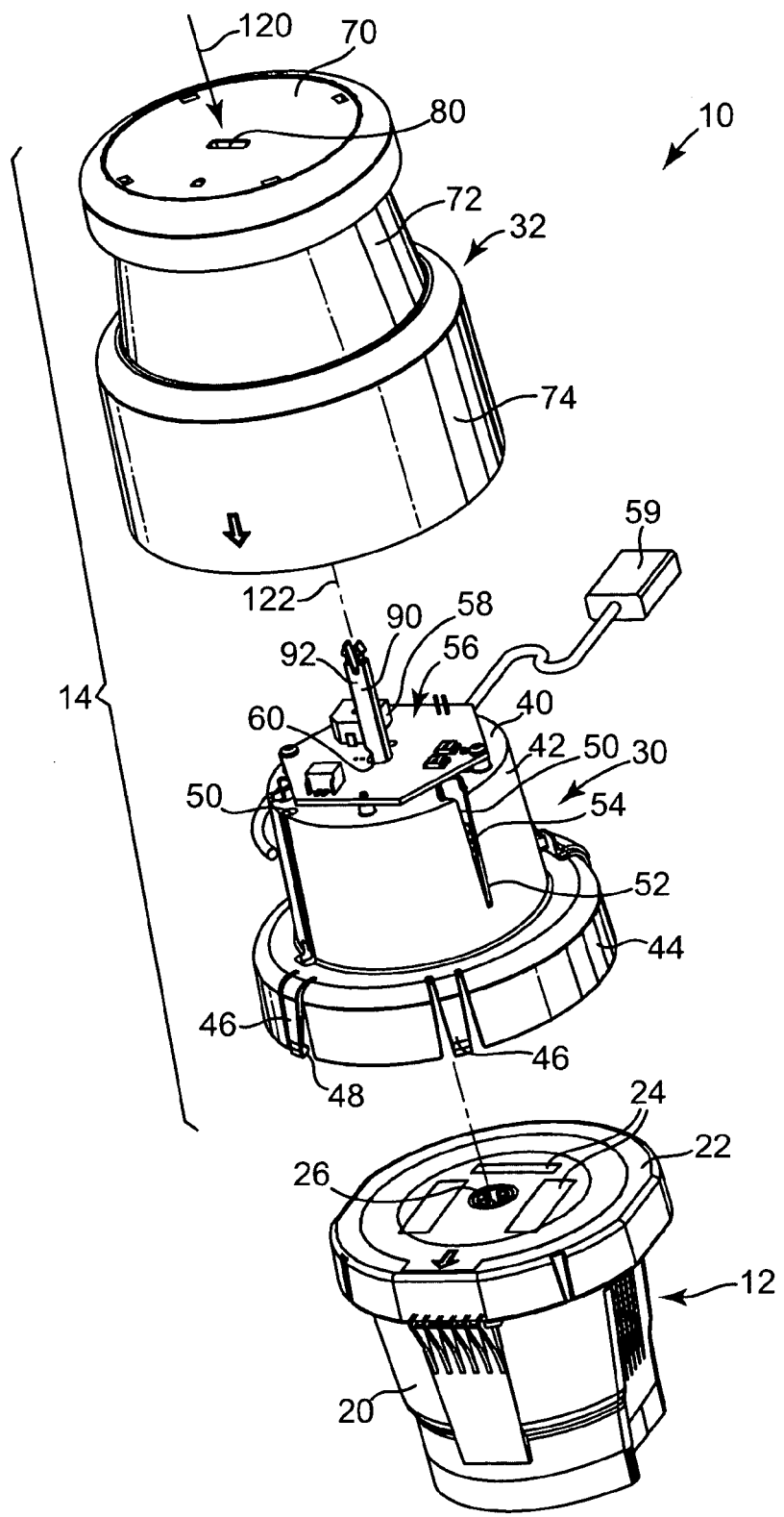
FIG. 1 is an exploded, perspective view illustrating one embodiment of a diagnostic test reader and sample container.

FIG. 1 illustrates an exploded, perspective view of one embodiment of a diagnostic test system generally at 10. In one embodiment, diagnostic test system 10 includes a sample cup 12 and a test reader 14. Sample cup 12 is configured to receive a test fluid from a patient and, in one embodiment, includes diagnostic assay strips configured to test the fluid for the presence of a particular analyte. Test reader 14 is configured to be selectively coupled with sample cup 12 to diagnostically asses assay strips within sample cup 12. In particular, test reader 14 is configured to be coupled and uncoupled with sample cup 12 in a push-push manner similar to that used with retractable ball point pens. When test reader 14 is pushed toward sample cup 12 a first time, test reader 14 is locked on sample cup 12. When test reader is pushed 14 toward sample cup 12 a second time, test reader 14 disengages and can be removed from sample cup 12.

Sample cup 12 includes any general cup, container, reservoir, or any other suitable fluid retaining system, such as a sponge or wick, 20 configured to receive a liquid sample, such as urine, blood, saliva, etc., from a patient. As such, container 20 is any suitable shape and style and is formed of any suitable material for retaining or maintaining the liquid sample. In one embodiment, sample cup 12 includes a lid 22 or other assay retaining member configured to be placed over container 20 enclosing the collected sample fluid between container 20 and lid 22. In one embodiment, lid 22 includes at least one assay 24 configured to interact with the sample fluid housed within container 20. Upon interaction with the sample fluid, each assay 24 indicates whether or not a particular analyte is present within the sample fluid. For example, each assay 24 may be configured to indicate the presence of an analyte indicating the patient is pregnant (such as human chorionic gonadotropin, or HCG) drug use of particular types of drugs, the presence of an infection causing bacteria, or any other suitable analytes. In one embodiment, lid 22 is substantially transparent such that assay 24 can be optically viewed through lid 22.

In one example, sample cup 12 is plunger aliquoted. Accordingly, sample cup 12 includes a cavity 26 extending from an outer surface of lid 22 into sample cup 12. A plunger or piston (not shown) is included in cavity 26. During use, the plunger is pushed further down into cavity 26 to effectively aliquot sample fluid stored in container 20 to contact assays 24 for testing.

Figure 2A:
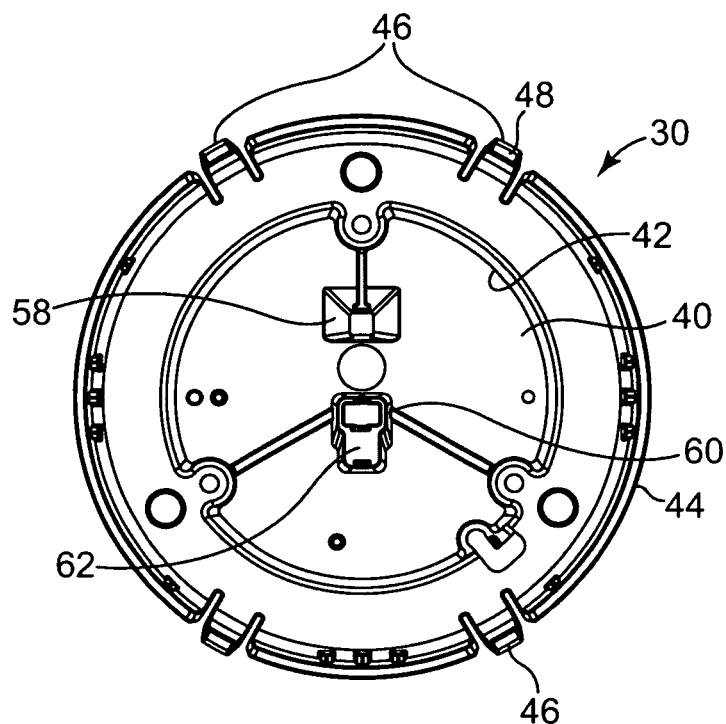
FIG. 2A is a bottom view illustrating one embodiment of an inner housing of the diagnostic test reader of FIG. 1.
Figure 2B:
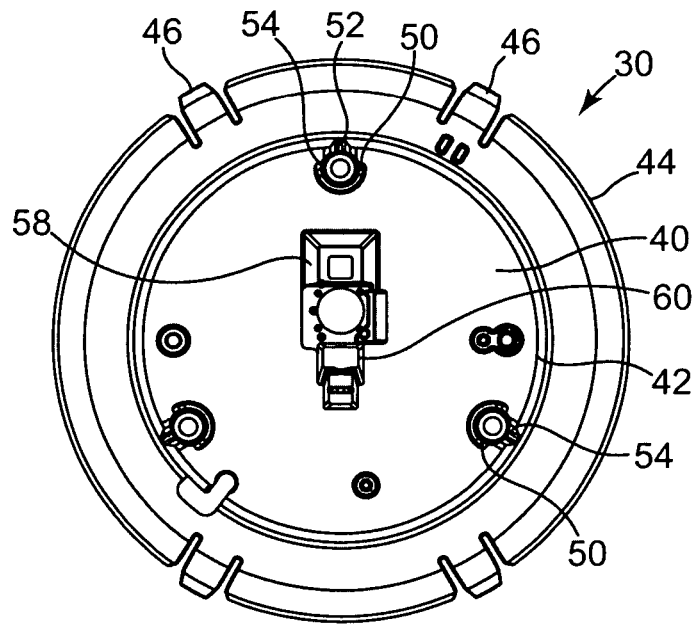
FIG. 2B is a top view of the inner housing of FIG. 2A.
Figure 3:
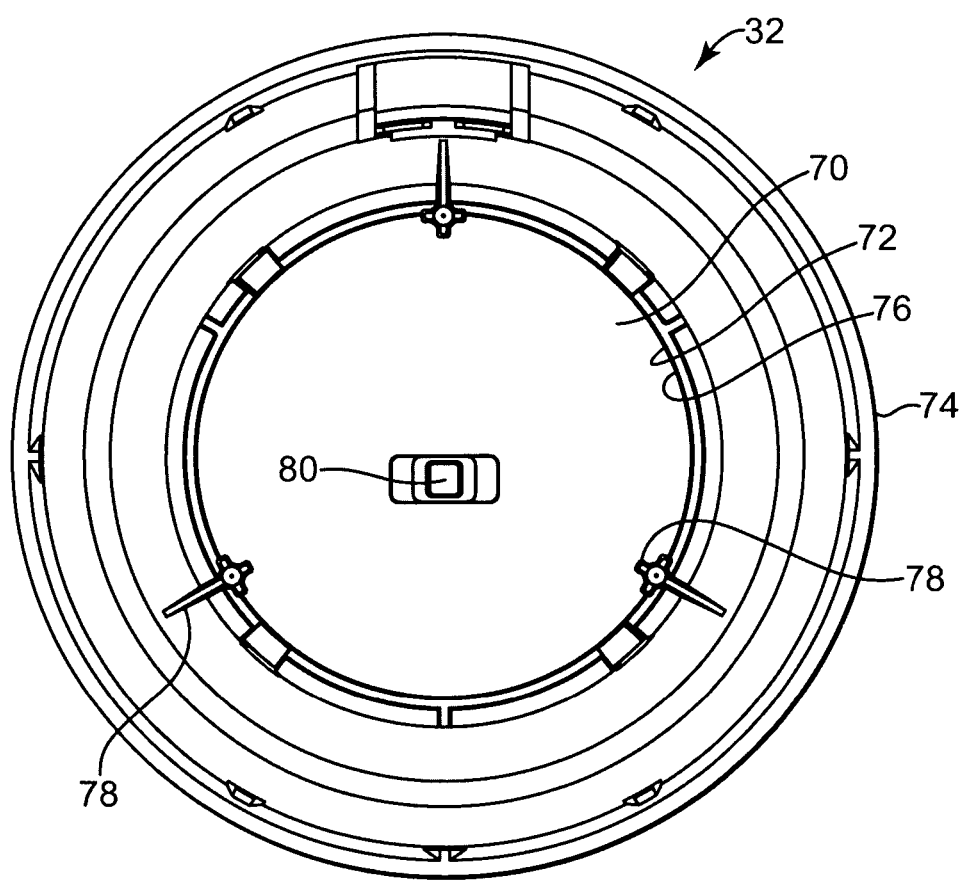
FIG. 3 is a bottom view illustrating one embodiment of an outer housing of the diagnostic test reader of FIG. 1.

In one embodiment, test reader 14 includes an inner housing 30 configured to receive sample cup 12 and an outer housing 32 configured to coaxially receive inner housing 30. Referring to FIGS. 1-3, inner housing 30 is substantially shaped as in inverted cup and, accordingly, defines a substantially circular and substantially planar top member 40 and a side wall 42 extending from and around the perimeter of top member 40. Top member 40 and side wall 42 collectively define a truncated conical or cylindrically shaped cup. In one embodiment, inner housing 30 extends radially outward and then further downward from side wall 42 opposite top member 40 to define a ring 44. Ring 44 is sized to fit around a perimeter of lid 22 of sample cup 12.

In one embodiment, ring 44 includes at least one tab 46, which defines a tooth 48 at an end opposite side wall 42 extending radially inward from the remainder of each tab 46. Each tab 46 is biased at least slightly outward (i.e., away from the center of inner housing 30, but is deformable so as to be moved or bent radially inward upon application of a suitable force to each tab 46. In one embodiment, a plurality of tabs 46 are included and are circumferentially spaced about ring 44.

In one embodiment, elongated, substantially cylindrical cavities 50 are formed through top member 40 and substantially parallel to side wall 42. In one embodiment, an elongated slit 52 is formed through side wall 42 and extends at least partially into a cavity 50. In one embodiment, a plurality of cavities 50 are evenly and circumferentially spaced relative to top member 40. In one embodiment, three cavities 50 are included and are spaced at approximately 120° intervals. Each cavity 50 is configured to receive a biasing member 54, such as a coil spring, or other suitable member. More specifically, spring 54 is coaxially positioned within cavity 50.

A test unit or circuitry 56 is secured to top member 40 on a side opposite the extension of side wall 42. Circuitry 56 includes or is in communication with the electrical components of test reader 14, such as an opto-electric camera, a processor, a timer, a memory, etc. In one embodiment, an opto-electric camera 58 is coupled with circuitry 56 and extends into inner housing 30 to optically capture images within or though inner housing 30. In one embodiment, a connection 59 to a computer processing unit (not shown) is coupled with circuitry 56. Connection 59 is any suitable connector, such as a USB cable, etc.

In one embodiment, an aperture 60 extends through top member 40. In one example, aperture 60 is substantially centered on top member 40. Aperture 60 is similarly formed with a rectangular or other suitably shaped perimeter.

Figure 5A:
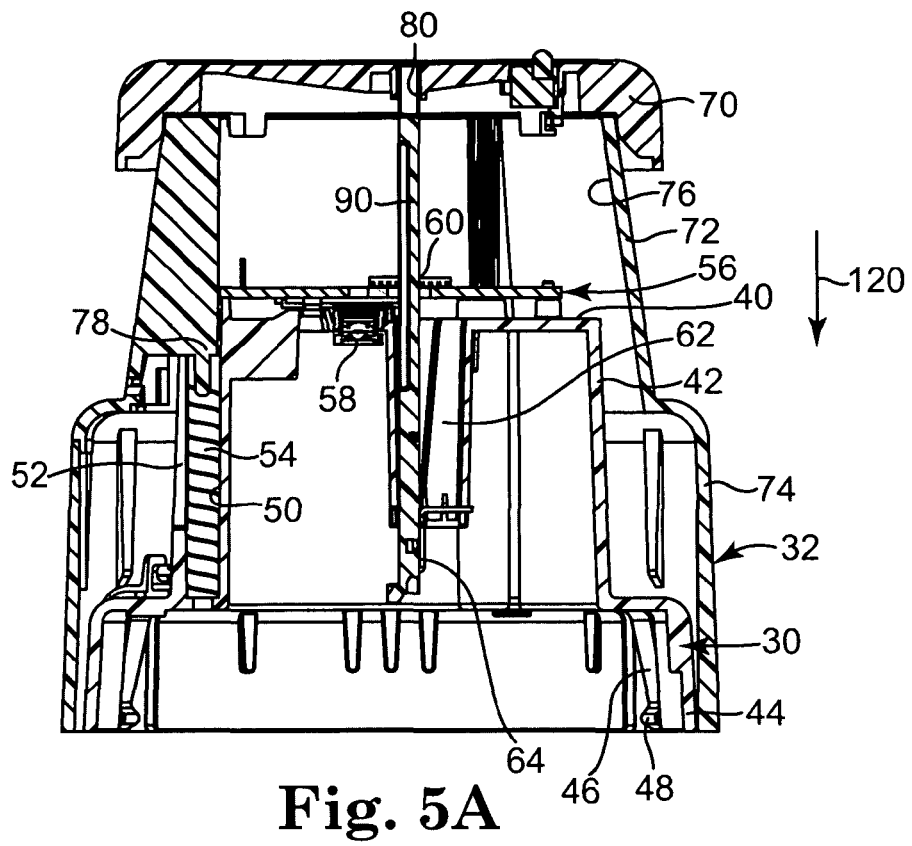
FIG. 5A is a cross-sectional view illustrating one embodiment of the diagnostic test reader of FIG. 1 in an unlocked position.

A pin support 62 protrudes from top member 40 into inner housing 30 as seen with additional reference to FIG. 5A. In one embodiment, pin support 62 is formed substantially adjacent to aperture 60. Pin support 62 is configured to receive a guide member or pin 64. In one embodiment, pin 64 is a small diameter, rigid rod. Pin 64 may be either linear or non-linear. In one embodiment, pin 64 resembles a three-legged S-shape. Pin 64 is mounted to pin support 62 opposite top member 40. In one embodiment, pin 64 is configured to rotate about its longitudinal axis while supported by pin support 62. Use of alternative guide members other than pin 64 that are suitable to ride along a track, as will be further described below, is also contemplated Outer housing 32 is substantially shaped as an inverted cup and is configured to coaxially receive inner housing 30 therein. Outer housing 32 includes a substantially circular top member or cap 70 and a truncated conical-shaped or cylindrically-shaped side wall 72 extending therefrom. Top member 70 and side wall 72 are separately formed and assembled or are integrally formed in a single piece. In one embodiment, outer housing 32 extends radially outward and then further downward from side wall 72 opposite top member 70 to defines a ring 74. In one example, ring 74 is sized to fit around ring 44 of inner housing 30 and side wall 72 is sized to fit around side wall 42 of inner housing 30.

Side wall 72 defines an inner surface 76. In one embodiment, side wall 72 defines at least one rib 78 extending radially inward from inner surface 76. The at least one rib 78 is positioned on inner surface 76 to correspond with a position of a cavity 50 and slit 52 of inner housing 30. Accordingly, when coupled together the at least one rib 78 extends into cavity 50 via slit 52 to guide the coaxial travel of inner housing 30 and outer housing 32. In one embodiment, a plurality of ribs 78 are evenly and circumferentially spaced on inner surface 76. In one embodiment, three ribs 78 are included and are spaced at approximately 120° intervals.

In one embodiment, top member 70 defines an aperture or notch 80 substantially centered on top member 70. In one example, aperture 80 has a substantially rectangular or square shape, although use of other suitable shapes is also contemplated.

Figure 4:
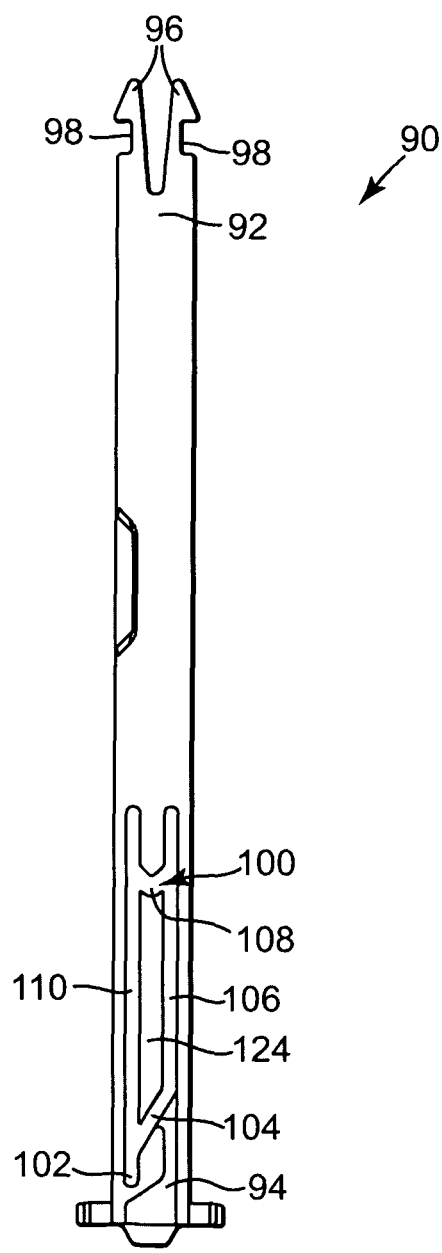
FIG. 4 is a side view illustrating one embodiment of an index member of the diagnostic test reader of FIG. 1.

In one embodiment, test reader 14 includes an index member 90 configured to facilitate selective coupling of outer housing 32 to inner housing 30 and of test reader 14 to sample cup 12. Referring to FIG. 4, in one embodiment, index member 90 is an elongated member defining a first or top end 92 and a second or bottom end 94. First end 92 of index member 90 resembles a fork having a two prongs 96. Each prong 96 is at least slightly deformable toward the other prong 96 while being biased to a nominal position as shown in FIG. 4. In one embodiment, each prong 96 defines a notch 98 on the outer side of each prong 96 (i.e., on the side opposite the other prong 96).

Near second end 92, index member 90 defines a track or channel 100. Channel 100 is configured to selectively receive pin 64. Accordingly, channel 100 has a width slightly larger than a diameter of pin 64. In one embodiment, channel 100 is formed as a closed loop and defines a nominal pin position 102, an angled portion 104, a first main leg 106, a locked pin position 108, and a second main leg 110. More specifically, in one example, angled portion 104 extends up and away from nominal pin position 102. First main leg 106 extends upward from angled portion 104 opposite nominal pin position 102 with a shallow inclined plane in the channel 100, which increases in height toward the top of first main leg 106 in the orientation illustrated in FIG. 4. Locked pin position 108 is positioned between main legs 106 and 110 and is positioned slightly below the top of each leg 106 and 110 in a stepped pocket below the inclined plane of the first main leg 106. Second main leg 110 is stepped down below the level of locked pin position 108 and extends down to nominal pin position 102 with an inclined plane increasing in height as toward the bottom of channel 100 in the orientation illustrated in FIG. 4. In one embodiment, second main leg 110 is substantially parallel to first main leg 106. Channel 100 is configured to act as a track for pin 64 to slide along in one-way travel as will be further described below.

Referring to FIGS. 1 and 5 collectively, during assembly of test reader 14, springs 54 are placed within cavities 50 of inner housing 30. In addition, index member 90 is placed partially through aperture 60 of inner housing 30. Pin 64 is placed within channel 100 of index member 90, in particular, is placed in channel 100 at nominal pin position 102. Pin 64 is not secured to channel 100 to be stationary within channel 100. Rather, pin 64 and all of inner housing 30 is slidably coupled with index member 90.

Outer housing 32 is coaxially aligned with and receives inner housing 30. When aligned, outer housing 32 is positioned such that ribs 78 of outer housing 32 are at least partially received within the respective cavities 50 and through slits 52 of inner housing 30 and to align aperture 80 with index member 90. Ribs 78 are positioned at least partially within the respective cavities 50 and interface with springs 54 maintained therein.

In one embodiment, index member 90 is coupled with outer housing 32. More specifically, fork end 92 of index member 90 interfaces with aperture 80 by bending prongs 96 toward one another and inserting the prongs at least partially through aperture 80. Once the bending force on prongs 96 is removed, prongs 96 widen back out to a nominal state. When in the nominal state, notches 98 each engage top member 70 to selectively secure index member 90 to outer housing 32. As such, index member 90 and outer housing 32 are coupled in a stationary manner, such that when outer housing 32 moves, index member 90 also moves.

Upon assembly, the biasing force of springs 54 generally maintains inner housing 30 and outer housing 32 spaced from one another as much as possible. Accordingly, pin 64 of inner housing 30 is generally maintained at the lowest possible point in channel 100, which in this case is nominal pin position 102. Assembled test reader 14 is configured to selectively receive sample cups 12 and to analyze assays 24 included therewith.

Figure 5B:
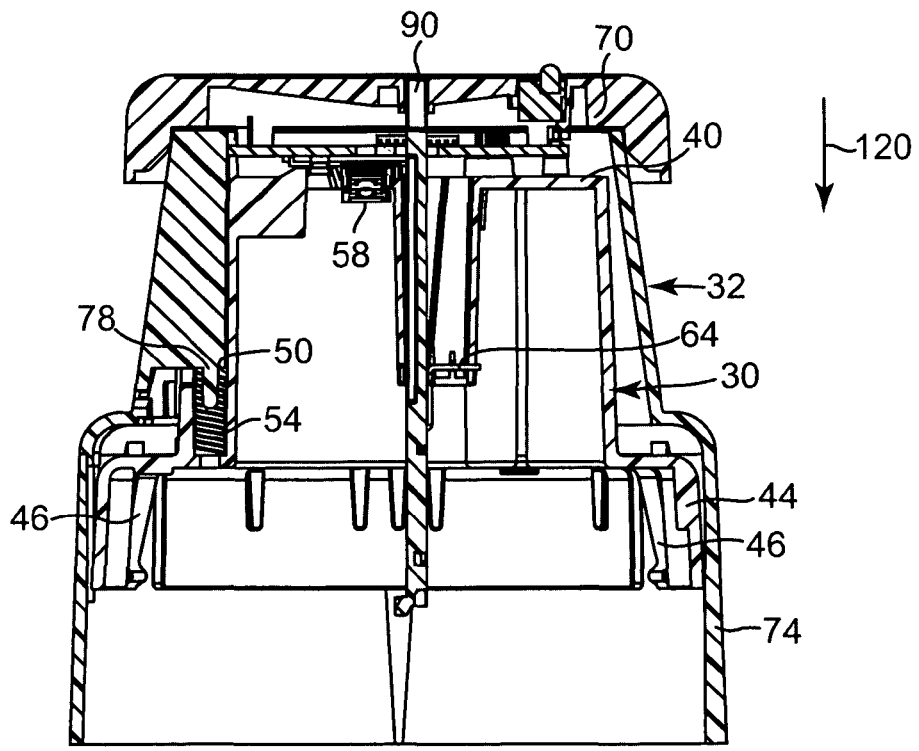
FIG. 5B is cross-sectional view illustrating one embodiment of the diagnostic test reader of FIG. 1 in a locked position.

During use of test reader 14, ring 44 of inner housing 30 is placed about lid 22 of sample cup 12. Since lid 22 includes assays 24, inner housing 30 is the assay interface of the test reader. Since tabs 46 of ring are biased outwardly, ring 44 easily slips over lid 22. Once test reader 14 is so positioned, a force generally indicated by arrow 120, which is substantially opposite the direction of biasing force, is applied to outer housing 32 to overcome the biasing force of springs 54, thereby, pushing housing 32 down over inner housing 30 to a locked position as illustrated in FIG. 5B. Notably, sample cup 12 is not illustrated in FIGS. 5A and 5B for clarity. In the locked position, ring 74 of outer housing 32 interacts with tabs 46 of inner housing 30, bending tabs 46 inward to grasp lid 22 of sample cup 12. Although primarily described herein a pushing test reader 14 toward sample cup 12, it should be understood that in one embodiment sample cup 12 is alternatively or additionally pushed toward test reader 14 in a direction opposite that indicated by arrow 120. In one embodiment, coupling test reader 14 with sample cup 12 includes test reader causing sample cap 12 to aliquot at least a portion of the sample fluid to assay 24. For example, upon coupling, index member 90 of test reader 14 moves into cavity 26 of sample cup 12 to active a plunger mechanism (not shown) to aliquot sample fluid stored in container 20 to assays 24.

In one embodiment, outer housing 32 is locked due to the interaction between pin 64 and index member 90. As previously described, forces from springs 54 are constantly trying to separate inner housing 30 from outer housing 32. Due to this force, pin 64 is initially forced to the lowest position in channel 100 that it can currently reside. As such, pin 64 begins in the lowest portion of channel 100, in other words nominal pin position 102.

When outer housing 32 is pushed in the direction generally indicated by arrow 120, which, in one embodiment, is parallel with a longitudinal axis of test reader 14 generally indicated in FIG. 1 at 122, the spring force is at least partially overcome moving outer housing 32 down over inner housing 30. As outer housing 32 moves down, so does index member 90. Accordingly, pin 64 of inner housing 30 translates to a higher position in channel 100. More specifically, referring to FIG. 4, pin 64 moves from nominal pin position 102, up angled portion 104, and up first main leg 106.

When the force 120 is removed, the spring forces are no longer impeded and pin 64 once again attempts to move to a lower position within channel 100. Due to the configuration of channel 100, pin 64 moves slightly downward and over to locked position 108. More specifically, the inclination and stepped nature of angled portion 104 and first main leg 106 generally prevent backsliding of pin 64 back down first main leg 106 ensuring pin 64 will continue to move one-way within channel 100 to locked position 108. Since this is the lowest point of channel 100 that pin 64 can find due to a block 124 surrounded by channel 100 and various ramps within channel 100, pin 64 is locked in position 108, and consequently, outer housing 32 is locked down upon inner housing 30. In this position, test reader 14 is fixed in position relative to and is able to analyze assays 24 of sample cup 12. In one embodiment, test reader 14 optically observes assay 24 with optoelectric camera 58 and analyzes any assay color change.

In one embodiment, when moved to the locked position, index member 90 is moved down into cavity 26 to interact with sample cup plunger (not shown) to aliquot at least a portion of the sample fluid within sample cup to interact with assays 24. As such, the assay test begins. In one embodiment, as plunger is moved, a mechanical, electric, or opto-electric switch is triggered and a timer included in circuitry 56 begins to countdown the amount of time required to complete the test or until any assay color change should be visible.

After assays 24 have been analyzed and read, sample cup 12 can be discarded. As such, a user once again applies a push force similar to push force 120 (i.e. in the same direction as the initial push force 120). The second push, moves outer housing 32 and index member 90 further down relative to inner housing 30. Once again, movement of pin 64 in one direction only due to the inclined and stepped nature of channel 100 as described above. As such, pin 64 is forced to a higher position in channel 100 and, therefore, moves from locked position 108 up and into second main leg 110 of channel 100. When second push force is removed, pin 64 once again moves in an attempt to find the lowest position in channel 100 due to the biasing force of springs 54 on outer housing 32 and as influenced by the steps and inclination within channel 100, namely within second main leg 100 and between first main leg 106, locked position 108 and second main leg 110. In particular, pin 64 moves down second main leg 110 back to nominal position 102. When in nominal position 102, test reader 14 returns to the nominal position illustrated in FIG. 5A. In the nominal position, outer housing 32 and inner housing 30 are sufficiently separated such that ring 74 is not longer positioned around ring 44. Therefore, tabs 46 of ring 44 are no longer pushed inward to grasp lid 22 of sample cup 12, thereby, releasing sample cup 12 to be removed from test reader 14 and to be properly discarded.

In view of the above, pin 64, channel 100, and biasing mechanism 54 collectively define a push-push locking mechanism configured to selectively lock or couple the diagnostic assay 24 relative to test reader 14. Notably, the first push and the second push are both applied to the outer housing 32 of test reader 14 and are both in a direction parallel to the longitudinal axis 122 of test reader 14 and to the direction of assembly between sample cup 12 and test reader 14. In view of the above, in one embodiment, no separate buttons need be pushed interacted with to lock and/or unlock test reader 14 from lid 22.

In the embodiments described above, the push-push locking mechanism utilizes a pin 64 and index member 90 interaction. However, any other suitable assembly or interaction can be used with biasing member 54 to form the push-push locking mechanism. For example, in one embodiment, a rotary index with interacting guide are combined with a biasing mechanism to form the push-push locking mechanism in a similar manner to retractable, ball point pens.

Figure 6A:
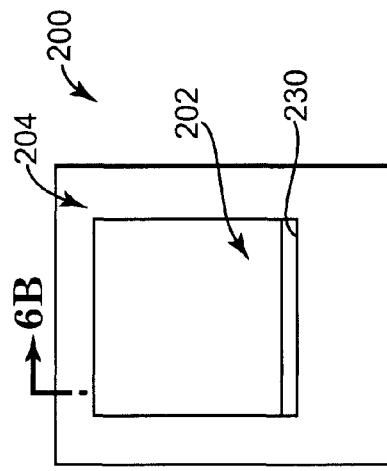
FIG. 6A is side view illustrating one embodiment of a diagnostic test reader and an assay assembly.
Figure 6B:
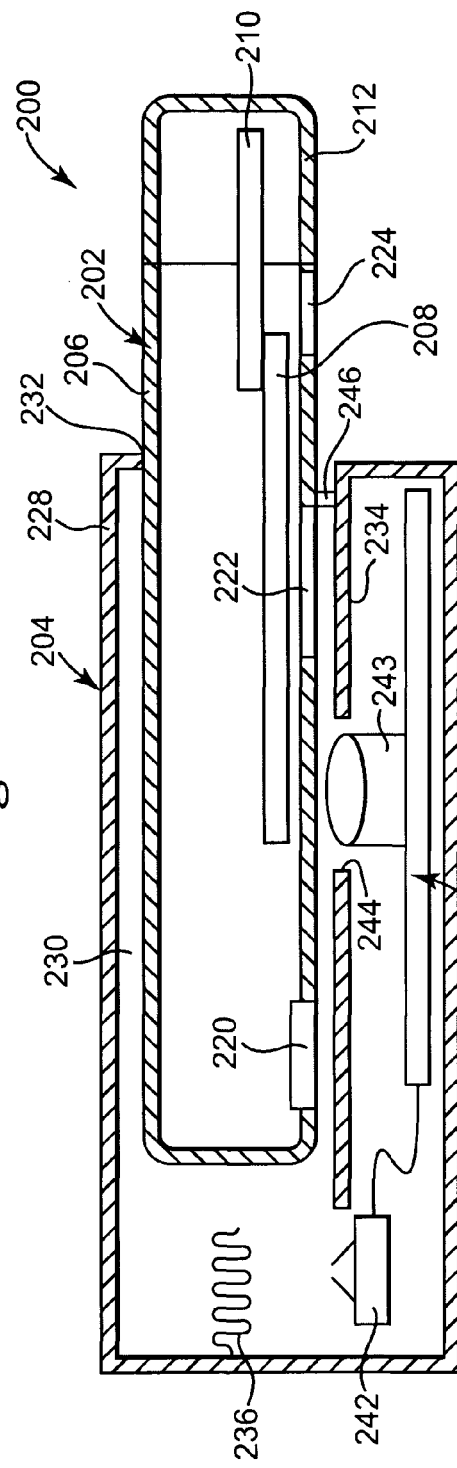
FIG. 6B is a cross-sectional view of FIG. 6A taken along the line 6B-6B.

Although described above as being a test reader interfacing with a sample cup, in other embodiments, the test reader may interface directly with the assay or with any other mechanism or assembly including the assay. For example, as illustrated in FIG. 6, in one embodiment, a diagnostic test system 200 includes an assay assembly 202 and a test reader 204. Assay assembly 202 includes a housing 206, an assay 208, a collection pad 210, and optionally, a cap 212.

Assay 208 is maintained within housing 206. Collection pad 210 contacts assay 208 and extends outside of housing 206. As such, a fluid sample or diluted solid sample (not shown) collected on collection pad 210 moves through collection pad 210 to assay 208 due to capillary action. In one embodiment, cap 212 is selectively coupled to housing 206 to enclose collection pad 210 before or after collection of a sample to prevent contamination of the sample or damage to collection pad 210.

In one embodiment, housing 206 defines a trigger 220 near an end opposite cap 212. Trigger 220 is configured to mechanically or electrically interact with test reader 204 to indicate proper position of assay assembly 202 within housing 206 as will be further described below. Housing 206 further defines a viewing window 222 and an aperture or channel 224. Viewing window 222 is aligned with a portion of assay 208 to allow optical viewing of assay 208 to assess any color change or other indication of an analyte in the sample through housing 206. Channel 224 is positioned near a cap end of housing 206 and, in one embodiment, is substantially similar to channel 100 described above. In one example, trigger 220, viewing window 222, and channel 224 are each longitudinally spaced along a single side of housing 206.

Test reader 204 includes a housing 228, which defines a cavity 230 having an opening 232 configured to receive assay assembly 202. In one embodiment, cavity 230 is at least in part defined by a support surface 234 configured to support assay assembly 202 within test reader 204. A spring or other biasing mechanism 236 is included in cavity 230 opposite opening 232. Spring 236 is configured to bias assay assembly 202 in an unlocked and releasable state.

In one embodiment, test reader 204 includes a test unit 240 and a switch 242. Test unit 240 includes an optical camera 243 or other assay assessing device. In one embodiment, a optical camera 243 is positioned opposite cavity 230 relative to support surface 234. However, support surface 234 includes an aperture or window 244 configured to permit test unit 240 to visually or otherwise access assay 208. Switch 242 is coupled with test unit 240 and is configured to interact with trigger 220 of assay assembly 202 to notify test unit 240 when assay assembly 202 is properly positioned within test reader 204 and ready for testing. In one embodiment, test reader 204 further includes a guide member, such as a pin 246 similar to pin 64 above, extending into cavity 230 and being configured to interface with channel 224 of assay assembly 202 as will be further described below.

During use, a sample is collected on collection pad 210 and cap 212 is coupled with housing 206 to enclosed collection pad 210. Sample collected by collection pad 210 moves via capillary action to assay 208 where assay 208 performs known chemical reactions in attempt to determine if an analyte is present within the collected sample. Assay assembly 202 with sample is placed through opening 232 and into cavity 230. In particular, assay assembly 202 is slid into cavity 230 until housing 206 interacts with and overcomes the bias of spring 236. Eventually, as housing 206 is slid relative to test reader 204 and after housing 206 begins to compress spring 236, pin 246 interfaces with channel 224. In one embodiment, channel 224 and pin 246 interact similar to channel 100 and guide member 64 described above to selectively lock and unlock the position of assay assembly 202 relative to test reader 204 due to the biasing force of spring 236 on a push-push basis.

Once assay assembly 202 is in a locked position (not shown) relative to test reader 204, trigger 220 contacts switch 242, which mechanically and/or electrically interact to notify test unit 240 that assay assembly 202 is in place and is ready to be analyzed. In one embodiment, when in the locked position, assay 208 and optical window 222 are positioned such that camera 243 can observe assay 208 for a color change or other visual indicator of the presence of a particular analyte within the sample in any suitable method. Test reader 204 may output the results of the analysis to any suitable display (not shown) or computer processing unit (not shown) for further analysis.

Following testing, assay assembly 202 is once again pushed toward test unit 204, or vice versa, to move pin 246 from a locked position in channel 224 to an unlocked position, thereby, releasing assay assembly 202 and allowing assay assembly 202 to be removed from test reader 204 in a similar manner as described above with respect to diagnostic test unit 10. As such, test reader 204 is ready to receive and analyze another assay within a similar assay assembly.

In view of the above embodiments and obvious variations thereof, a diagnostic test system is described for electrically analyzing an assay. In general, a test reader is configured to receive an assay strip or assay containing device in a push-push manner. The push-push manner allows the test reader to be easily locked in place during testing. By locking test reader in place relative to the diagnostic assay during testing, optoelectric camera or other device is held over or interacts with the assay at a constant position, which will generally translate to improved test results. The push-push locking mechanism further allows for the assay to be easily removed from the test reader at the completion of the test. Accordingly, the disposable test reader is configured for ease of receipt and disposal of each tested assay. As such, the disposable test reader as described in the embodiments above, provides an intuitive, reliable, repeatable method to mate a point-of-care test reader and assay for aliquot and analysis of a test sample.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A diagnostic test reader comprising:
    an assay interface that receives a diagnostic assay;
    a locking mechanism that locks the diagnostic assay within the assay interface in response to one of the diagnostic assay and the diagnostic test reader being directly given a first manual push in a first direction toward the other of the diagnostic assay and the diagnostic test reader, and to unlock the diagnostic assay within the assay interface in response to the one of the diagnostic assay and the diagnostic test reader being directly given a second manual push in the first direction;
    a sample cup that receives a liquid sample from a patient;
    an index member that aliquots at least a portion of the liquid sample to the diagnostic assay when the diagnostic assay is locked in the assay interface; and
    a test unit that analyzes the diagnostic assay.

2. The diagnostic test reader of claim 1, further comprising: a biasing mechanism adapted to bias the diagnostic assay in an unlocked position relative to the assay interface.

3. The diagnostic test reader of claim 2, wherein the biasing mechanism applies a biasing force in a second direction that is substantially opposite the first direction.

4. The diagnostic test reader of claim 2, wherein the locking mechanism is adapted to lock the biasing member in a compressed position in response to the first push.

5. The diagnostic test reader of claim 1, wherein the locking mechanism includes a track defined within the chamber and a guide member adapted to move within the track between a nominal position and a locked position, and wherein the diagnostic assay is locked within the diagnostic test reader when the guide member is in the locked position.

6. The diagnostic test reader of claim 1, wherein the diagnostic assay is maintained by a retaining member and the assay interface receives the diagnostic assay by receiving the retaining member.

7. The diagnostic test reader of claim 6, wherein the locking mechanism interacts with the retaining member to lock and unlock the diagnostic assay within the assay interface.

8. The diagnostic test reader of claim 1, further comprising an inner housing configured to be selectively locked around the diagnostic assay and an outer housing configured to coaxially receive the inner housing.

9. The diagnostic test reader of claim 8, wherein the first push translates the outer housing from a first position over the inner housing to a second position where the outer housing extends further over the inner housing in the first position than in the second position.

10. The diagnostic test reader of claim 9, wherein when in the second position, the outer housing locks the inner housing to the diagnostic assay, and wherein the second push moves the outer housing from the second position to the first position.

11. The diagnostic test reader of claim 1, wherein the first direction is parallel to a longitudinal center axis of the diagnostic test reader.

12. The diagnostic test reader of claim 1, wherein the diagnostic assay is inserted into the assay interface by moving the one of the diagnostic assay and the diagnostic test reader in the first direction.

13. A method of employing a diagnostic assay and a test reader, the method comprising:
    coupling a diagnostic assay with a test reader by manually moving one of the diagnostic assay and the test reader in a first direction toward the other of the diagnostic assay and the test reader;
    aliquoting a test sample onto the diagnostic assay, wherein coupling of the diagnostic assay and the test reader transfers a liquid sample from a sample cup to the diagnostic assay; and
    uncoupling the diagnostic assay from the test reader by manually pushing one of the diagnostic assay and the test reader in the first direction.

14. The method of claim 13 further comprising: analyzing the diagnostic assay with the test reader to determine if an analyte is present within the test sample; wherein aliquoting and analyzing are performed after coupling the diagnostic assay with the test reader and before uncoupling the diagnostic assay from the test reader.

15. The method of claim 13, further comprising: biasing the diagnostic assay to be uncoupled with the test reader, and wherein coupling the diagnostic assay with the test reader includes overcoming the bias on the diagnostic assay.

16. The method of claim 13, wherein coupling the diagnostic assay with the test reader includes moving an outer housing of the test reader further over an inner housing of the test reader causing the inner housing to secure the diagnostic assay in place relative to the test reader.

17. The method of claim 16, wherein the inner housing secures the diagnostic assay by grasping a retaining device containing the diagnostic assay.

* * * * *

UNITED STATES PATENT AND TRADEMARK OFFICE
CERTIFICATE OF CORRECTION

| | | |
|---|---|---|
| PATENT NO. | : 8,491,850 B2 | Page 1 of 1 |
| APPLICATION NO. | : 11/313091 | |
| DATED | : July 23, 2013 | |
| INVENTOR(S) | : Baugh et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1147 days.

Signed and Sealed this
Twenty-third Day of December, 2014

Michelle K. Lee
*Deputy Director of the United States Patent and Trademark Office*